United States Patent [19]
Ferguson Hugo S.

[11] Patent Number: 5,481,086
[45] Date of Patent: Jan. 2, 1996

[54] HIGH TEMPERATURE DEFORMABLE CRUCIBLE FOR USE WITH SELF-RESISTIVELY HEATED SPECIMENS

[75] Inventor: Ferguson Hugo S., Averill Park, N.Y.

[73] Assignee: Dynamic Systems Inc., Poestenkill, N.Y.

[21] Appl. No.: 287,954

[22] Filed: Aug. 9, 1994

[51] Int. Cl.⁶ .................................................. F27D 11/00
[52] U.S. Cl. .......................... 219/385; 219/390; 392/388
[58] Field of Search ................................ 219/385, 390, 219/403, 420, 426, 455, 456, 458, 459, 469, 523–524, 528–529, 549, 550; 73/790, 826, 828, 824; 392/388, 389

[56] References Cited

U.S. PATENT DOCUMENTS

| | | | |
|---|---|---|---|
| 2,694,922 | 11/1954 | Vilella | 73/15.6 |
| 3,401,226 | 9/1968 | Renkey | 13/35 |
| 3,539,769 | 11/1970 | Barker | 219/275 |
| 3,589,166 | 6/1971 | Klar et al. | 73/15.6 |
| 3,637,980 | 1/1972 | Fox et al. | 392/389 |
| 3,735,011 | 5/1973 | Soykan | 13/35 |
| 3,936,587 | 2/1976 | Sitek et al. | 13/23 |
| 4,049,250 | 9/1977 | Schmidt | 266/275 |
| 4,205,047 | 5/1980 | Thubeauville | 422/242 |
| 4,242,553 | 12/1980 | Frosch et al. | 219/10.49 R |
| 4,247,735 | 1/1981 | Rigatti-Luchini | 13/25 |
| 4,393,718 | 7/1983 | Gebhard et al. | 73/859 |
| 4,424,956 | 1/1984 | Grant et al. | 266/248 |
| 4,646,504 | 3/1987 | Britvec | 52/648 |
| 4,687,343 | 8/1987 | Raffalski | 374/56 |
| 4,759,215 | 7/1988 | Atchley et al. | 73/167 |
| 5,015,825 | 5/1991 | Brindley | 219/390 |
| 5,179,622 | 1/1993 | Kleyer | 392/389 |
| 5,195,378 | 3/1993 | Ferguson | 73/790 |

Primary Examiner—Tu Hoang
Attorney, Agent, or Firm—Peter L. Michaelson; John C. Pokotylo

[57] ABSTRACT

A deformable, inexpensive crucible for use with a dynamic thermo-mechanical physical test or simulating system, specifically for holding a self-resistively heated specimen (250) at liquid temperatures and particularly, though not exclusively, one suited for use in simulating thin-strip continuous casting processes. The crucible is formed of a thermally and electrically insulating material (222) which surrounds, e.g., the bottom and two opposing and sides of the specimen perpendicular to the direction of the force used for compression and which, in turn, is held within a thin, readily deformable, e.g., U-shaped shell (210) with an upwardly facing open portion. The shell is appropriately sized with a length and height less than that of insulating material such that, when properly positioned over the material, the shell will not contact the specimen and hence remain insulated from the heating current flowing therethrough and thus will not exhibit any self-resistive heating. The insulating material develops a sufficiently large thermal gradient thereacross such that, when a central region (260) of the specimen located on one side of the material is at liquid temperatures, the temperature of the shell located on other side of the material will remain sufficiently below its liquidus temperature, such that the shell, at its elevated temperature, will still possess adequate mechanical strength to mechanically support the liquid or semi-solid portion of the specimen. Advantageously, the shell can be manufactured from the same or similar low-cost material as the specimen.

16 Claims, 4 Drawing Sheets

HIGH TEMPERATURE DEFORMABLE CRUCIBLE FOR USE WITH SELF-RESISTIVELY HEATED SPECIMENS

BACKGROUND OF THE DISCLOSURE

1. Field of the Invention

The invention relates to a deformable inexpensive crucible for use with a dynamic thermo-mechanical test or simulating system, specifically such a crucible for holding a self-resistively heated specimen at liquid temperatures while the specimen is being controllably deformed in compression or tension, and one preferably, though not exclusively, suited for use in simulating thin-strip continuous casting processes.

2. Description of the Prior Art

Generally speaking, steel materials are fabricated in a mill through a multi-step process. Once the necessary raw materials, including pig iron, are gathered, molten steel is first cast into a desired starting shape. During a casting process, pig iron is typically heated to liquefaction, and appropriate alloying and other raw materials are then added to produce a desired composition. The resulting liquid metal, i.e. liquid steel, is then poured into a mold and cast into a desired shape. With current equipment, casting is done on a continuous basis, such that a single strand of metal is produced from liquefied steel. This strand may take the form of a slab, sheet, wire or other special shape, such as I-beams, angles or channels, as defined by a mold then in use. During continuous casting, the walls of the mold which confine the liquefied steel are cooled to a temperature below the solidification temperature of the steel. As a result, as the external surfaces of the strand, which abut against the walls of the mold, freeze while the central region of the strand remains liquid. Through solidification, the surface provides sufficient strength to the strand to maintain its shape. Inasmuch as liquid metal can be continuously poured into the mold from a tundish (an intermediary vessel from which liquid steel is directed into the mold) while the strand exits from the mold, the strand takes on a continuous shape. Once cast and appropriately cooled, the strand may be coiled, if in the form of sheet or wire, or cut to a desired length(es), if the strand is in the form of a thick slab or other special shape.

After a strand is fabricated, it is then typically rolled to a desired intermediate thickness, generally through a stand of several rolling mills, typically using both hot and cold rolling processes. Each mill imparts a given reduction in thickness to the strand while increasing its length. This overall rolling process may provide a considerable reduction in thickness. For example, for strands on the order of 10 inches (approximately 25 cm) in thickness, a roll stand may well reduce this strand to sheet only 0.04 inch (approximately 0.1 cm) thick, for a total reduction of 250. For ease of reference, this process will be referred to as "thick-slab" casting. Unfortunately, rolling mills, particularly those intended for rolling relatively thick materials, are physically huge and inordinately expensive, with each particular roll stand consuming a substantial amount of energy. Moreover, since various rolling characteristics change the underlying morphology of the rolled material and thus affect the physical properties of the resulting metallic sheet, such as in terms of material temperature, sheet strain and strain rate and sheet flatness, each roll stand must be precisely controlled.

Consequently, given the difficulties in reducing relatively thick strands of continuously cast steel, stainless steel or other such materials, the art has turned to the use of so-called thin-strip continuous casting. This form of casting produces strands that are considerably thinner than those previously used, typically on the order of only 10% or less than that of a thick slab, such as a strip 1 inch thick (approximately 2.5 cm) or less rather than 10 inches as had occurred previously with thick slab casting. The exiting cast strip from a continuous caster is typically "semi-solid", i.e. a portion of the cast material, typically its outer surfaces, is solid while the remainder is liquid. Deforming a semi-solid material can be advantageously accomplished quite easily and with substantially less energy than deforming the same sized, though solid, strip.

Thus, by using relatively thin strands, such as, e.g., a oneinch (approximately 2.5 cm) thick cast metallic strip, significant savings accrue to the mill owner in terms of needing fewer roll stands and associated production equipment, less physical space, less deformation and hence substantially less energy to roll the strand to the desired thickness than with thick-slab casting. Furthermore, as contrasted with thick-slab cast materials, thin-strip casters, by virtue of producing thin strip at relatively high lineal rates and hence, subjected to relatively high cooling rates (to properly freeze the surfaces), advantageously produces final material with a relatively small size grain and without a need for subsequent heat treatment. Consequently, steel manufacturers prefer using thin-strip rather than thick-slab continuously cast materials.

However, not only does thin-strip casting exacerbate problems already inherent in thick-slab casting, it also presents a variety of new problems. The former includes changes in material segregation brought about by inclusions of foreign materials in the cast strand as well as by high rates of solidification.

Since thin-strip casting relies on using fewer rolling stands to reach a final sheet thickness than does thick-slab casting processes, much less mechanical work is imparted to a thin strand than a thick slab. Inasmuch as each reduction changes and further refines the microstructure of the strand, relatively few roll stands, as used in a thin-strip casting process, yields decreased grain refinement over that occurring in a thick-slab casting process. Consequently, owing to a lessened number of roll stands, the desired properties of the final strip must be developed by changing some of variables in the casting process itself along with those applicable to the roll stand that imparts a final reduction.

In order to properly set the appropriate process variables, the dynamics of the thin-strip continuous casting and rolling processes must be properly understood. Doing so entails gaining knowledge of the thermal and mechanical properties of the cast material while it is solidifying, including the time the material is semi-solid, and thus how, during that time, the material can be treated, thermally and/or through deformation, to yield a desired set of properties. For example, the relationships of time at temperature, as well as temperature itself and solidification rate, to resulting material properties are all critically important.

In practice, "thin-strip" continuous casting (as with other physical manufacturing processes, such as rolling or forging, utilize very costly production equipment, which, for economic considerations, often requires that this equipment be commercially and profitably used as much as possible—with little, if any, use made available for research and experimentation. As a result, sufficient operational data on, inter alia, thin-slab continuous casting processes, while essential for proper understanding and eventual control of the process, has proven to be very costly to obtain from actual production equipment.

In the past, the other physical manufacturing processes presented the same commercially-induced difficulties in readily providing cost-effective process data. Accordingly and with respect to those processes, the art has turned to employing equipment which accurately and dynamically, and highly cost-effectively, simulates the operation of such a process but on a relatively small metallic specimen, measures the consequent physical affect(s), e.g. dilation, on the specimen that results from the simulated process and then provides resulting specimen measurement data for subsequent inspection and analysis. In this instance, the specimen takes the place of a considerably larger workpiece; the simulation equipment functions as a considerably scaled down, though accurately controllable, version of the desired process. Provided the simulation is sufficiently accurate, the data will reflect the affect(s) of the corresponding physical manufacturing process(es) on a metallic workpiece. One such piece of equipment, which provides very accurate, dynamic thermo-mechanical simulation and testing of a specimen, is the GLEEBLE 2000 system (manufactured by the present assignee which also owns the registered trademark "GLEEBLE"). This system, under computer control, self-resistively heats a metallic specimen according to a desired thermal program to establish, in the specimen, a desired longitudinal thermal profile with transverse isothermal planes. Simultaneously, the system imparts a desired deformation profile to the specimen and obtains physical measurement data, such as, e.g., dilation, therefrom. In simulating a physical manufacturing process, the simulator is programmed to simultaneously impart the same thermal and mechanical deformation profiles to the specimen as the process, e.g., rolling, forging or extruding, would be expected to impart to a workpiece. Hence, the specimen would exhibit, though at a reduced scale, the same temperature gradients and strain direction(s) as the process would be expected to produce in the workpiece. Advantageously, not only is simulation highly cost-effective, generally by several orders of magnitude, as compared to use of actual production equipment in a test environment and the associated cost of "down time", but also a simulator allows many more variables to be selectively and accurately controlled and then precisely measured than would be possible on actual production equipment. This latter factor often permits improvements to be made in the process, resulting material or both.

In the GLEEBLE 2000 system, a solid specimen is longitudinally held between two opposing electrically conductive jaws or anvils. One of the jaws is controllably and longitudinally moveable with respect to the other to impart a desired axial tensile/compressive force, resulting in a desired deformation profile, to the specimen. Coincident with such movement or not, a controlled electrical heating current can be serially passed from one jaw, through the specimen to the other jaw to self-resistively heat the specimen to a desired thermal profile.

With the relatively recent and pronounced interest in using a thin-strip continuous casting process and the pronounced advantages, including economic, of using simulation, the steel industry, inter alia, is attempting to employ dynamic thermal-mechanical physical simulators to characterize this process in much the same manner as these simulators have been used to assess other physical processes, such as rolling.

However, with specimens existing in a semi-solid state as would occur during simulated thin-strip continuous casting, a serious problem arises as to how to hold the specimen within the physical simulator, such as the GLEEBLE 2000 system. Part of the time the specimen is in the semi-solid state, a workzone of the specimen may be partly liquid and partly solid, or entirely liquid. While the workzone remains in either of these states, the specimen must be supported in some fashion. Furthermore, since semi-solid strip exiting from a continuous thin-strip caster is often rolled to a given thickness, the specimen must be held, while still semi-solid, such that it can be deformed. Doing so would typically entail holding the specimen in some manner such that as the specimen were to be compressed (squeezed) along one direction, the specimen could expand along another direction perpendicular to the direction of the force used for compression. Inasmuch as the specimen is semi-solid, the compressive force would be very small; as contrasted with a relatively large force required to compress the specimen while it was totally solid.

This problem is compounded by the need for such a crucible that not only holds the specimen but simultaneously permits it to be self-resistively heated such that, e.g., the GLEEBLE 2000 system can be used to simulate the thin-strip continuous casting process.

Clearly then, what is needed for simulating thin-strip continuous casting processes is a proper crucible: one that appropriately supports a semi-solid self-resistively heated specimen and surrounds enough of it to hold the specimen shape before, during and after the simulation. Conventional high-temperature crucibles known in the art for use with liquid metallic specimens were manufactured from quartz or other materials, such as suitable ceramics, that remained solid at temperatures well above the melting point of the specimen.

Unfortunately, conventional high-temperature crucibles suffer various serious drawbacks which either completely or at least partially preclude their use with thin-strip continuous casting simulations.

First, crucibles made from, e.g., quartz and ceramic based materials, are brittle and readily fracture when deformed. Accordingly, if such a crucible were to hold a molten or partly melted specimen, then, when subsequently deformed—even slightly, the crucible would fracture and a liquid portion of the specimen would spill from the fractured crucible. Hence, once the crucible fractured, the simulation would be abruptly halted and any simulation results, based on further deformation, frustrated. Moreover, quartz crucibles also tend to be quite expensive, typically on the order of approximately $10.00 or more each.

Second, since the simulation involves deforming the semi-solid specimen, each individual simulation would also destroy the crucible. While various high temperature metals, such as tantalum, exist in the art and from which a crucible could be formed, particularly one that will deform well and not fracture, these metals are also very expensive. For example, one crucible constructed from sufficiently thin tantalum sheet may cost upwards of $50.00 or more. Properly assessing the behavior of a casting process may involve use of a significant number of specimens, often hundreds if not more. Clearly, if expensive crucibles were to be used, with one per each specimen, the added cost of the crucibles themselves may inhibit extensive simulation, over large numbers of specimens, and thus economically preclude completely characterizing the casting process of interest, ultimately to the detriment of the mill owner.

Therefore, while a pressing demand exists for equipment that can accurately and cost-effectively simulate a continuous thin-strip casting process, a specific problem in the art must first be solved before that demand can be addressed: a low-cost, deformable crucible must be provided to properly and completely hold a self-resistively heated specimen, at liquid temperatures with a semi-solid or liquid portion, before, during and after the simulation. Advantageously, such a crucible would readily permit dynamic thermo-mechanical simulating and test systems, such as the GLEEBLE 2000 system, to be used in accurately simulating thin-strip continuous casting processes.

SUMMARY OF THE INVENTION

Accordingly, an object of the invention is to provide a deformable high temperature crucible for use in simulating, e.g., a thin-strip continuous casting process with a dynamic thermo-mechanical physical test or simulating system.

Another object is to provide such a crucible that will properly support a specimen, at liquid temperatures and with a liquid or semi-solid portion, during simulation of the thin-strip continuous casting process.

An additional object is to provide such a crucible that is very low-cost, as contrasted with conventional high-temperature crucibles heretofore used with molten metallic specimens.

A further object is to provide such a crucible that can hold a self-resistively heated specimen in such a system and during such a simulation.

My present invention advantageously achieves these and other objects and overcomes the deficiencies inherent with conventional crucibles known in the art. In that regard, the inventive crucible is low cost, deformable and particularly suited for use in holding a self-resistively heated specimen, where the specimen is gripped at both of its ends by an opposing pair of jaw assemblies and has a liquid or semi-solid centrally heated region.

In accordance with my inventive teachings, the crucible is formed of a thermally and electrically insulating material, e.g. a silica cloth, and a relatively thin mechanical shell. The insulating material surrounds, e.g., the bottom and two opposing sides of the specimen adjacent to the bottom and thus, when installed on the specimen, takes on, e.g., a U shape. Alternatively, the shell may take on other cross-sectional shapes to conform to that of the specimen. The shell, having a shape similar to that of the insulating layer, is positioned over the insulating material with its opening facing upwards. The shell is appropriately sized with a length and height less than that of insulating material such that, when properly positioned over the insulating material, the shell will not contact the specimen and hence remain insulated from the heating current flowing therethrough and thus will not exhibit any self-resistive heating.

The shell may be made from the same (or similar) low-cost material as the specimen without losing needed mechanical stability required to confine the liquid portion within a working (central) region of the specimen. The insulating material can be any one of a wide variety of flexible and inexpensive thermally and electrically insulating materials. However, the insulating material must be one that can develop a sufficiently large thermal gradient thereacross such that, when a central region of the specimen located on one side of the insulating material is at a liquid temperature, the temperature of the shell located on other side of this material will remain sufficiently below its liquidus temperature so that the shell, even at its elevated temperature, will still possess sufficient mechanical strength to mechanically support the liquid (or semi-solid) portion of the specimen. In addition, this insulating material must also be sufficiently tight, i.e. with a maximal porosity, such that none of the liquid specimen will permeate through the material and contact the shell.

Inasmuch as the only appreciable heat source is the self-resistively heated specimen itself, the temperature of the shell is governed by conductive heat transferred from the specimen and through the insulating material as well as heat loss from the shell itself. As a result of constructing the shell from thin material, e.g. 0.88 mm (approximately 0.035 inch) thick (or less), into a U-shape, the shell, which is easily deformable, has a relatively large exposed surface area and a thin cross-section. Consequently, a substantial heat loss occurs from the shell itself. By using an insulating material that can tolerate a sufficiently large thermal gradient thereacross, the shell, even if manufactured from the same or similar material as the specimen, remains at a much lower temperature than the specimen and still properly retains the specimen, with a liquid or semi-solid central region. Alternatively, the shell could be manufactured from a material having a lower melting point than the specimen provided the insulating material maintains the temperature of the shell sufficiently below its melting point, even when the central region of the specimen is at liquid temperatures, to present sufficient mechanical rigidity to properly support the semi-solid portion of the specimen.

In accordance with a feature of my invention, in those instances where the specimen needs to be cooled at an increased rate, such as during solidification measurements, the crucible can be readily removed from the specimen, once the surfaces of the specimen have sufficiently cooled and a solid skin has formed around the central region sufficient to support the weight of the liquid or semi-solid interior of the specimen. Once the crucible has been removed, a cooling spray, mist or gas can be directed at the specimen to provide an increased cooling rate. The crucible is readily removed by means of a hook, engaged with a flange extending outwardly and downwardly from the shell, that is moved downward while the specimen is being gripped by the simulating system.

BRIEF DESCRIPTION OF THE DRAWINGS

The teachings of the present invention can be readily understood by considering the following detailed description in conjunction with the accompanying drawings, in which.

To facilitate understanding, identical reference numerals have been used, where possible, to designate identical elements that are common to the figures.

DETAILED DESCRIPTION

After considering the following description, those skilled in the art will clearly realize that the teachings of my invention can be readily utilized in any of a wide variety of thermo-mechanical systems for holding a metallic specimen, particularly, though not exclusively, one that is self-resistively heated to a semi-solid state. In essence, a specimen heated in my inventive crucible can be elevated up to and including its liquidus temperature and can be mechanically deformed in place or after removal of the crucible even though some of the material inside the specimen may still be in a liquid state. Since the present invention is particularly suited for use with holding electrically conductive test specimens in a GLEEBLE 2000 ("GLEEBLE" is a registered trademark of the present assignee) dynamic thermo-mechanical physical test or simulating system and particularly one being used for simulating a thin-strip continuous casting process, then, for simplicity and ease of understanding, I will discuss my present invention in that context.

Figure 1:
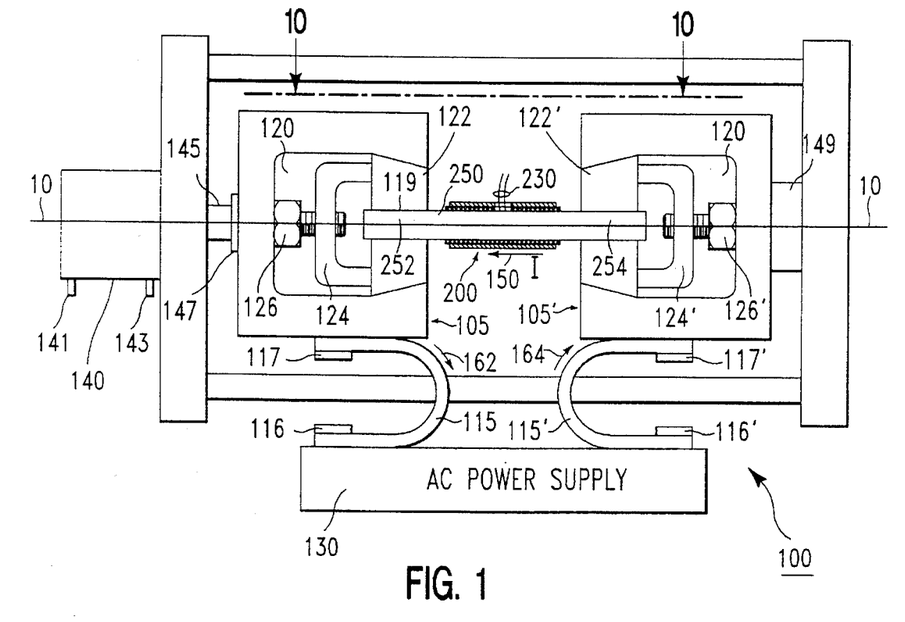
FIG. 1 depicts, in schematic form, a top view of test stand 100 that forms part of a dynamic thermo-mechanical physical simulating system, such as the GLEEBLE 2000 system, utilizing my inventive crucible and configured for simulating the performance of a thin-slab continuous casting process.

FIG. 1 depicts, in schematic form, a top view of test stand 100 that forms part of the GLEEBLE 2000 system. As shown, this system uses my inventive crucible in conjunction with simulating a thin-slab continuous casting process.

As depicted, specimen 250 is held between two identical jaw assemblies 105 and 105', both of which are mounted in load frame 110, with the specimen and both jaw assemblies being coaxially aligned along common longitudinal axis 10. Jaw assembly 105' is stationary, being securely mounted, coaxially via load cell 149, to the load frame. The load cell accommodates relatively little movement, typically on the order of 0.0039 inch (approximately 0.1 mm) for a full load. Jaw assembly 105 is mounted, via insulating disk 147, to a distal end of piston rod 145 axially extending from hydraulic cylinder 140. As a result of the controlled lateral movement of the piston, in response to hydraulic fluid being forced by a suitable servo-controlled hydraulic system (well known and not shown), under suitable pressure via hydraulic inlet and outlet ports 141 and 143, respectively, jaw assembly 105 accurately moves laterally and coaxially towards or away from jaw assembly 105' thereby imparting either a compressive or tensile force to the specimen situated therebetween. The precise distance through which the piston rod moves is governed by a predetermined deformation profile stored within a computer and associated control circuitry (all of which is well known and not shown) that forms part of the simulating system and is connected to test stand 100.

Both of the jaw assemblies are connected through collectively flexible leads 115 and 115' to high current, low voltage alternating current (AC) power supplied by AC power supply 130. These leads are secured to opposite terminals of the power supply through fasteners, typically bolts, bolts 116, 116', 117 and 117' to jaw assemblies 105 and 105', respectively. This supply provides a source of AC heating current (I) that self-resistively heats specimen 250. During operation and specifically throughout one-half cycle of applied AC power, the heating current serially flows from power supply 130, through flexible lead 115', in the direction of arrow 164, through jaw assembly 105', and into one end of specimen 250 Within the specimen, the current uniformly flows in the direction of arrow 150. Upon exiting from the specimen, current flows through jaw assembly 105, through flexible lead 115 and in the direction shown by arrow 162, back into power supply 130. The direction of current flow reverses with each successive half-cycle of applied AC power. Insulating disk 147 prevents any of the heating current from flowing into piston rod 145 and, from there into hydraulic cylinder 140.

Within jaw assemblies 105 and 105', wedge jaw pairs 122 and 122', respectively, mechanically hold specimen 250 within identical wedge portions of the jaw assemblies. Each of these jaw assemblies has an external wedge taper, on the order of approximately 10 degrees with respect to the longitudinal axis of the specimen, that matches an internal complementary wedge taper on the jaw assemblies. Each wedge assembly has an internal channel, e.g., channel 119, which abuttingly and peripherally encircles one end of the specimen, and is parallel to the axis of the specimen. Each end, i.e. ends 252 and 254, of a specimen, with a rectangular cross-section, is simply inserted into the channel in one of the wedge portions. During specimen insertion, this channel has a rectangular cross-sectional opening that is slightly larger than the cross-section of the specimen. Once the specimen is inserted into wedge portions in each of the jaw assemblies, each wedge portion is inserted into a wedge pocket into the corresponding jaw assembly and then mechanically locked into position. The latter is accomplished through jacks 120 and 120', which are formed of U-shaped member 124 and 124' into which jack screws 126 and 126', respectively, are threaded (the internal threads are not shown). In particular, as each jack screw, such as screw 126, is tightened, the rotation of the screw pushes the corresponding U-shaped member, through which the screw is threaded, against and, thus, mechanically forces, an associated wedge pair, such as wedge pair 122, to abuttingly slide against the internal taper of the jaw assembly. Thus, owing to the complementary tapered surfaces on both the wedge pairs and jaw assemblies, the wedge pairs become mechanically locked in place within the jaw assemblies and, due to resulting compression of the wedge pairs, both specimen ends lock in place within the wedge pairs. Test stand 100 itself, and as thusfar described, does not form part of the present invention. Hence, for further information on the test stand, the reader is referred to, e.g., U.S. Pat. No. 5,195,378 entitled "Dynamic Thermal-Mechanical Material Testing System Utilizing a Balanced Field" and issued Mar. 23, 1993 (and co-owned by the present assignee hereof) which is incorporated by reference herein.

Figure 10:
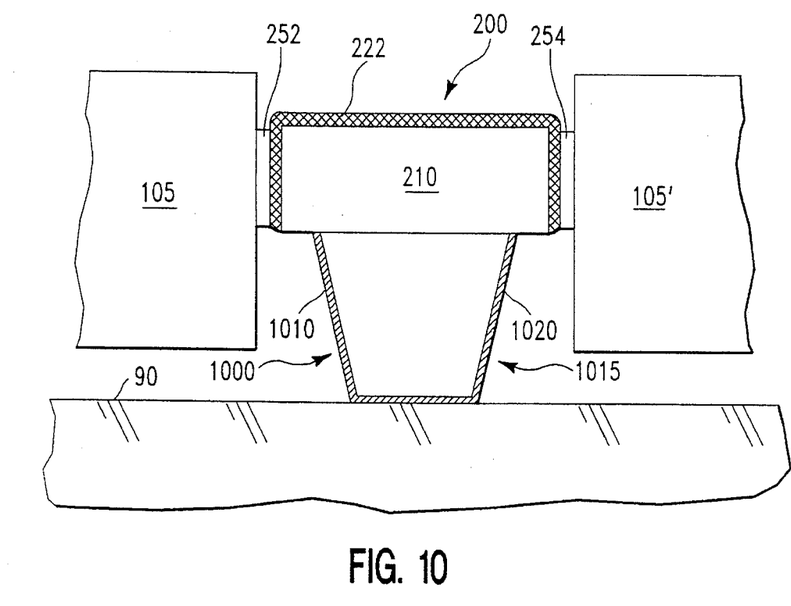
FIG. 10 depicts a side view of a support that can used with test stand 100, taken along lines 10—10 as shown in FIG. 1, to support both a specimen, of rectangular cross-section, and my inventive crucible.

Once the specimen is locked in place and before any simulation is begun, inventive crucible 200 (which is discussed in detail below in conjunction with FIGS. 2-4) is installed on the specimen. As will be discussed, inventive crucible 200, in its preferred embodiment, for a steel specimen, is formed of a thermally insulating cloth, such as a silica cloth, along with an external steel shell, the latter being illustratively form of the same material as is the specimen. To install the crucible, the silica cloth is first placed around three sides of the specimen, specifically along a bottom surface of the specimen and extending up opposing side surfaces adjacent to the bottom, with sufficient care such that the steel shell when placed over the cloth will not contact the specimen. The steel shell is then positioned, from the bottom of the specimen upward, onto the cloth. Once the crucible is properly placed on the specimen, a suitable support, such as U-shaped support 1000 shown in FIG. 10, is positioned (propped in place) between a ground plane (typically the floor of a vacuum chamber which houses the jaw assemblies) of the test stand and the crucible to prevent the crucible from sliding off the specimen during subsequent deformation. As shown in FIG. 10, which depicts a side view of one, rather simple, embodiment of this support, support 1000 is positioned between ground plane 90 and the crucible. As shown, support 1000 is formed of U-shaped piece 1005 appropriately bent to have two upwardly extending diverging legs 1010 and 1020. The width of the support and a divergence angle of the legs are all not critical. Illustratively, the support is fabricated from 0.035 inch (approximately 0.089 cm) thick type 304 austenitic stainless steel. This material has been cold rolled to approximately a ½ hard condition and possesses some spring-like qualities. As such, during installation of the support, legs 1010 and 1020 are temporarily bent outward to permit the support to be positioned between the crucible and the ground plane. Thereafter, the spring effect of the support will keep the support tightly in place against both the ground plane and the crucible. When a central region (e.g. region 260 shown in FIG. 2) of the specimen becomes liquid, the specimen ends will still remain solid, due to conductive heat loss through the wedge portions and jaw assemblies. Hence, through support 1000, the crucible will remain in place on the specimen during its subsequent deformation. Not only can the support be fabricated to have any one of a wide variety of different shapes, but also any one of a wide variety of different supporting mechanisms other than that shown in FIG. 10, i.e. specifically supporting the bottom of the crucible upward from the ground plane, can be used in lieu of support 1000.

Returning to FIG. 1, the heating current serially passing through the specimen self-resistively heats the specimen. Parts of the test stand that may heat due to the current flow, such as the flexible leads and jaw assemblies, are water cooled to maintain a relatively low temperature and thus prevent undue thermal expansion. The specimen, which is not water cooled, heats uniformly due to the current flow therethrough, with iso-thermal planes established therein. The relatively cool jaw assemblies, as contrasted with a central region of the specimen, conducts heat out of the ends of the specimen thereby establishing a thermal gradient near each end of the specimen. Consequently, when the specimen is heated such that the temperature of a central region (e.g. region 260 shown in FIG. 2) of the specimen reaches the melting point of the specimen, that portion turns to liquid which is held by the crucible. Reducing the heating current permits additional heat loss at the ends of the specimen as well as surface heat losses therefrom to occur. If these losses are sufficient, then the temperature of this region of the specimen will fall below the melting point and thus this region of the specimen will change back to a solid.

After the central region of the specimen completely liquefies or assumes a semi-solid state, as desired, stand 100 is instructed, under computer control, to controllably and accurately move jaw assembly 105, relative to jaw assembly 105', over a pre-defined distance(s) and with a pre-defined acceleration(s) to impart a desired deformation profile to the specimen. This profile may involve applying one or a sequence of controlled compressive and/or tensile forces across the specimen in order to yield a given strain and strain rate in the specimen representative of, e.g., those which would occur in a thin-strip continuous caster. During this time, the heating current may also be simultaneously varied, again under computer control, to accurately impart a desired thermal profile to the central region of the specimen then being deformed.

Figures 2, 3, 4:
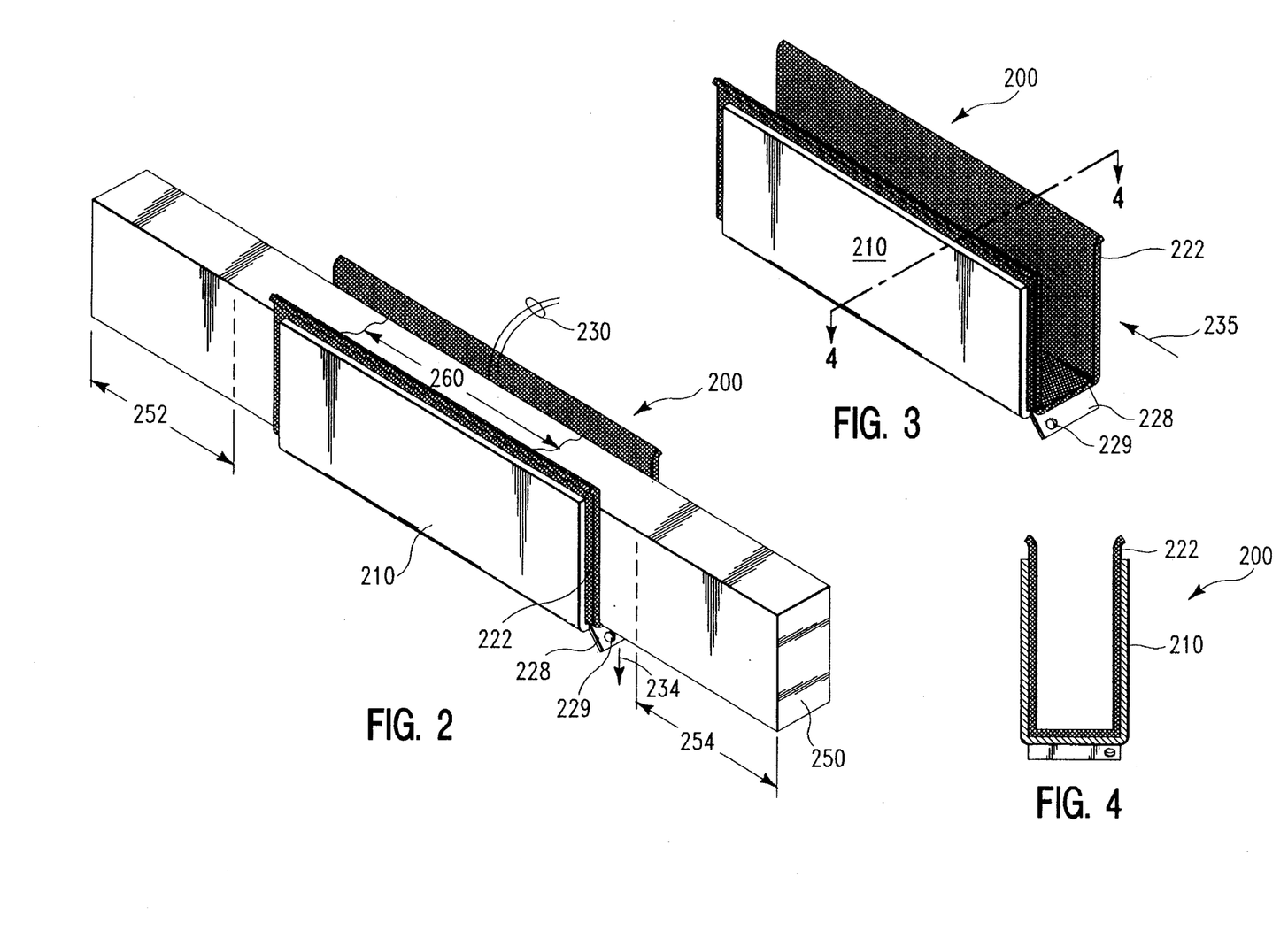
FIG. 2 depicts a perspective view of one embodiment of my inventive crucible, i.e. crucible 200, holding an illustrative metallic specimen in the form of a relatively narrow rectangular bar, all as shown in FIG. 1.
FIG. 3 depicts a perspective view of my inventive crucible 200, shown in FIGS. 1 and 2.
FIG. 4 depicts a cross-sectional view of my inventive crucible 200, the cross-section being taken along a plane perpendicular to a longitudinal axis of the crucible, containing lines 4-4 shown in FIG. 3 and viewed in the direction of arrow 235 shown therein.

FIG. 2 depicts a perspective view of inventive crucible 200 holding metallic specimen 250, shown in FIG. 1. To facilitate understanding, throughout the following discussion, the reader should also simultaneously refer to FIGS. 3 and 4 which respectively show perspective and cross-sectional views solely of crucible 200. As depicted in these figures, my inventive crucible is formed of thermally and electrically insulating material, e.g. silica cloth, 222 and thin mechanical shell 210. The insulating material surrounds the bottom and two opposing sides adjacent to the bottom of the specimen and thus, when installed on the specimen, takes on a U-shape. U-shaped shell 210 is positioned over the insulating material with an open portion of the shell extending upward. The shell is appropriately dimensioned with a length and height less than that of insulating material 222 such that, when properly positioned over the material, the shell will not contact the specimen and hence remain insulated from the heating current flowing therethrough. Shell 210 may be made from the same material as the specimen. For example, if the specimen is SAE 1018 carbon steel and is to be heated to its melting temperature in central region 260, then shell 210 may be made of the same steel alloy without losing needed mechanical stability required to confine the liquid or semi-solid portion within region 260 of the specimen. The insulating material can be any one of a wide variety of flexible and inexpensive thermally and electrically insulating materials. However, the insulating material must be one that can develop a sufficiently large thermal gradient thereacross such that, when the central region of the specimen located inward of and on one side of insulating material 222 is at liquid temperatures, the temperature of the shell located on the other side of this material will remain sufficiently below its liquidus temperature so that the shell will possess sufficient mechanical strength, even at its elevated temperature, to mechanically support the liquid or semi-solid central region of the specimen. In addition, this insulating material must also be sufficiently tight, i.e. with a maximal porosity, such that none of the liquid specimen will permeate through the material and contact the shell. One such preferred material that can be used for insulating material 222 is a 0.75 mm (approximately 0.029 inch) tightly woven silica cloth manufactured by Thermal Material Systems, Inc. of Byron, California.

Inasmuch as insulating material 222, e.g. silica cloth, electrically insulates shell 210 from specimen 250, thus preventing heating current from flowing in the shell, the shell does not exhibit any self-resistive heating. Hence, the temperature of the shell is governed by conductive heat transferred through the insulating material as well as heat loss from the shell itself. Furthermore, owing to the large exposed surface area of the shell and its small mass, particularly its thin cross-section, the shell exhibits a substantial heat loss. Inasmuch as specimen 250 is the only source of heat, by providing a sufficiently large thermal gradient across the insulating material, the shell, even if manufactured from the same or similar material as the specimen, remains at a substantially lower temperature than the specimen, particularly that of central region 260, and still properly retains the specimen, with a liquid or semi-solid central region. Alternatively, the shell could be manufactured from a material having a lower melting point than the specimen provided, that when the central region of the specimen is at liquid temperatures, the insulating material maintains the temperature of the shell sufficiently below its melting point to present adequate mechanical rigidity to properly support the semi-solid or melted central region of the specimen.

The temperature of central region 260 of specimen 250 is measured illustratively by a thermocouple (well known and not specifically shown) having leads 230. These leads are connected to control circuitry (not shown) that forms part of the GLEEBLE 2000 system. The thermocouple is placed along a wall of the specimen and situated between the specimen and insulating material 222. Alternatively, specimen temperature may be measured by a variety of other techniques, including pyrometry.

For a specimen of SAE 1018 carbon steel 0.48 inch (approximately 12 mm) wide by 0.79 inch (approximately 20 mm) deep, I constructed a crucible formed of a sheet of 0.75 mm (approximately 0.029 inch) tightly woven silica cloth which confines two sides and the bottom of the specimen. This sheet, in turn, is surrounded by a steel shell of SAE 1018 steel 0.034 inch (approximately 0.88 mm) thick. Through experimentation, I found that when the central region of the specimen is heated to its liquidus temperature in air (over 2550° F., in excess of approximately 1400° C.), the temperature of the shell rises to approximately 1800° F. (approximately 1000° C.). This latter temperature is sufficiently low such that the shell, even at this elevated temperature, still retains enough mechanical strength to confine the specimen, including its liquid or semi-solid portion.

Furthermore, thin steel used in shell 210, such as the 0.88 mm thick steel, is readily deformed. The insulating material, e.g. silica cloth, provides essentially no mechanical strength. Hence, specimen 250 contained within the crucible, either in a liquid or semi-solid state, is easily deformed, with relatively little force, by relative movement of the jaw assemblies within the test stand. Even after multiple deformations, e.g. compressions, the crucible retains its deformed shape.

As contrasted with a conventional quartz crucible costing approximately $10.00 each or tantalum crucibles costing upwards of $50.00 each or more, I estimate that inventive crucible 200 will cost substantially less: approximately $0.25 each or less, with the silica cloth, as specified above, to be approximately $0.20 or less to fit a typical sized specimen, and a steel shell to be approximately $0.05 each or less.

The length of central region 260 of the specimen 250, which at temperature is either liquid or semi-solid, is determined by the amount of electrical energy supplied by means of the heating current. As described above, specimen ends 252 and 254 are gripped by the jaw assemblies (see FIG. 1). Inasmuch as the jaws are water cooled as noted above, the specimen ends lose thermal energy through conduction into the jaw assemblies. As such, a thermal gradient appears at both ends of the specimen and extends inward to central region 260 shown in FIG. 2. The extent of this gradient defines the length of region 260. When properly configured and at an equilibrium melting temperature, the GLEEBLE 2000 system sets up an energy balance of thermal losses and gains such that thermal losses from the specimen through conduction, convection and radiation matches the amount of energy supplied to the specimen per unit time by the system.

In some instances, the thermal losses from the top surface of region 260 may be too large during an initial phase of specimen solidification. To limit such losses, insulating material 222 can be extended from both sides of the specimen across the top of region 260 to fully encircle and thus insulate region 260.

Alternatively, in other instances that occur with solidification during continuous casting, the cooling rate exhibited by specimen 250 may be too slow. Owing to the insulating effect of insulating material 222 situated at least partially around the specimen, a water spray or other coolant directed against the specimen may not sufficiently increase the cooling rate. Advantageously, crucible 200 may be removed using a hook (not shown) moved by a suitable puller (also not shown) such as a pneumatic cylinder. Here, the hook would be threaded into hole 229 contained within flange 228, the latter being connected to, or formed as illustratively a downwardly facing extension of, a lower end of shell 210 and extending across its width. Accordingly, once the specimen has cooled sufficiently to freeze and hence form a solid skin around region 260 which, in turn, will adequately support the liquid or semi-solid interior of the specimen, the puller, while the specimen remains gripped between the jaw assemblies, can simply exert an appropriately directed force, such as downward, in the direction of arrow 234, on flange 228, to pull the entire crucible off the specimen. Of course, any crucible support, such as support 1000 (see FIG. 10), would be removed prior to removing the crucible. A simple clip or other simple fastener (well known and not shown) can be used to attach insulating material 222 to shell 210 such that both of these items are removed at the same time. Removing the entire crucible will expose a substantially increased surface area of the specimen, basically its entire working length, which, in turn, will permit the specimen, either by itself or quenched in some manner, e.g. through a gas, water or mist spray, to cool at an increased rate. Such an increased rate may be needed to accurately match and hence simulate the cooling rates commonly found in a continuous casting mill.

Figures 5, 6, 7:
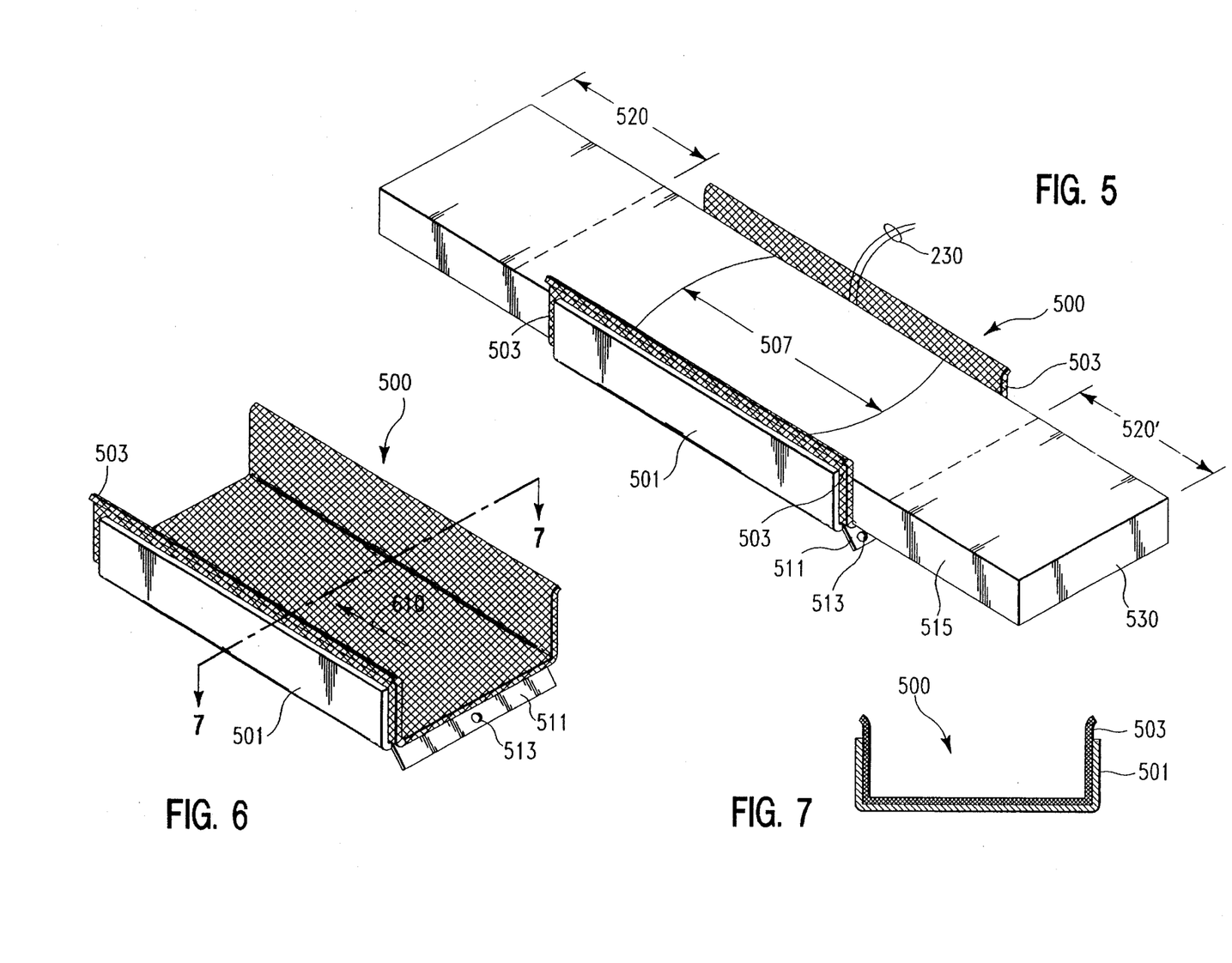
FIG. 5 depicts an alternate embodiment of my inventive crucible, i.e. here crucible 500, holding a specimen in the form of a relatively wide rectangular bar—as contrasted with specimen 250 shown in FIG. 2.
FIG. 6 depicts a perspective view of my inventive crucible 500 shown in FIG. 5.
FIG. 7 depicts a cross-sectional view of my inventive crucible 500, the cross-section being taken along a plane perpendicular to a longitudinal axis of the crucible and containing lines 7—7 shown in FIG. 6 and viewed in the direction of arrow 610 shown therein.

FIG. 5 depicts an alternate embodiment of my inventive crucible for holding a specimen in the form of a relatively wide rectangular bar—as contrasted with specimen 250 shown in FIG. 2. To facilitate understanding, throughout the following discussion, the reader should also simultaneously refer to FIGS. 6 and 7 which respectively show perspective and cross-sectional views solely of crucible 500. In some continuous casting simulations, a need may arise to preferentially cool the specimen from one surface. As depicted in these figures, particularly FIG. 5, specimen 530 is formed to have a relatively wide top surface. Crucible 500 is formed of insulating material 503 held in place by shell 501, both of these items being manufactured of the corresponding material described above. Flange 511 having hole 513 illustratively extends from a lower end of shell 501 and across its entire width. Inasmuch as large surface dimension of the specimen is exposed through the crucible, this surface may be cooled by an appropriate spray, e.g. water, gas or mist, to rapidly cool central region 507, which, similar to region 260 of specimen 250 (see FIG. 2), will have been heated to a liquid or semi-solid state. Alternatively and similarly to specimen 250, specimen 530 (shown in FIG. 5) can cool to where a skin forms around central region 507 to fully support the weight of the liquid or semi-solid interior of the specimen. Once this occurs, a hook, as described above, threaded through hole 513 in flange 511, can then be used, along with a clip or other connection between the shell and the insulating material all as described above, to remove the entire crucible from the specimen. Hence, with entire specimen 530 then exposed, the specimen can be radiationally cooled by itself or intentionally quenched to increase the overall cooling rate.

Solidification is affected by gravity. Hence, use of specimens, both with an extended dimension (as between specimen height, or thickness, and width), such as shown in FIG. 5 and without, as shown in FIG. 2, as well as with associated crucibles, permits gravity to affect solidification along a preferential direction. In this regard, the affect on solidification will occur with either the large dimension of the specimen being vertical, as shown in FIG. 2, or horizontal, as shown in FIG. 5. While the specimens shown in these figures have a modest difference in height and width, in actuality and in relatively new mills, the thickness of continuously cast thin-strip may be only a few millimeters, while the width of the strip may be several meters. With such a wide dimensional difference, specimen orientation will likely be a very important factor in the study of the resulting microstructures obtained from the solidification and deformation processes.

Figures 8, 9:
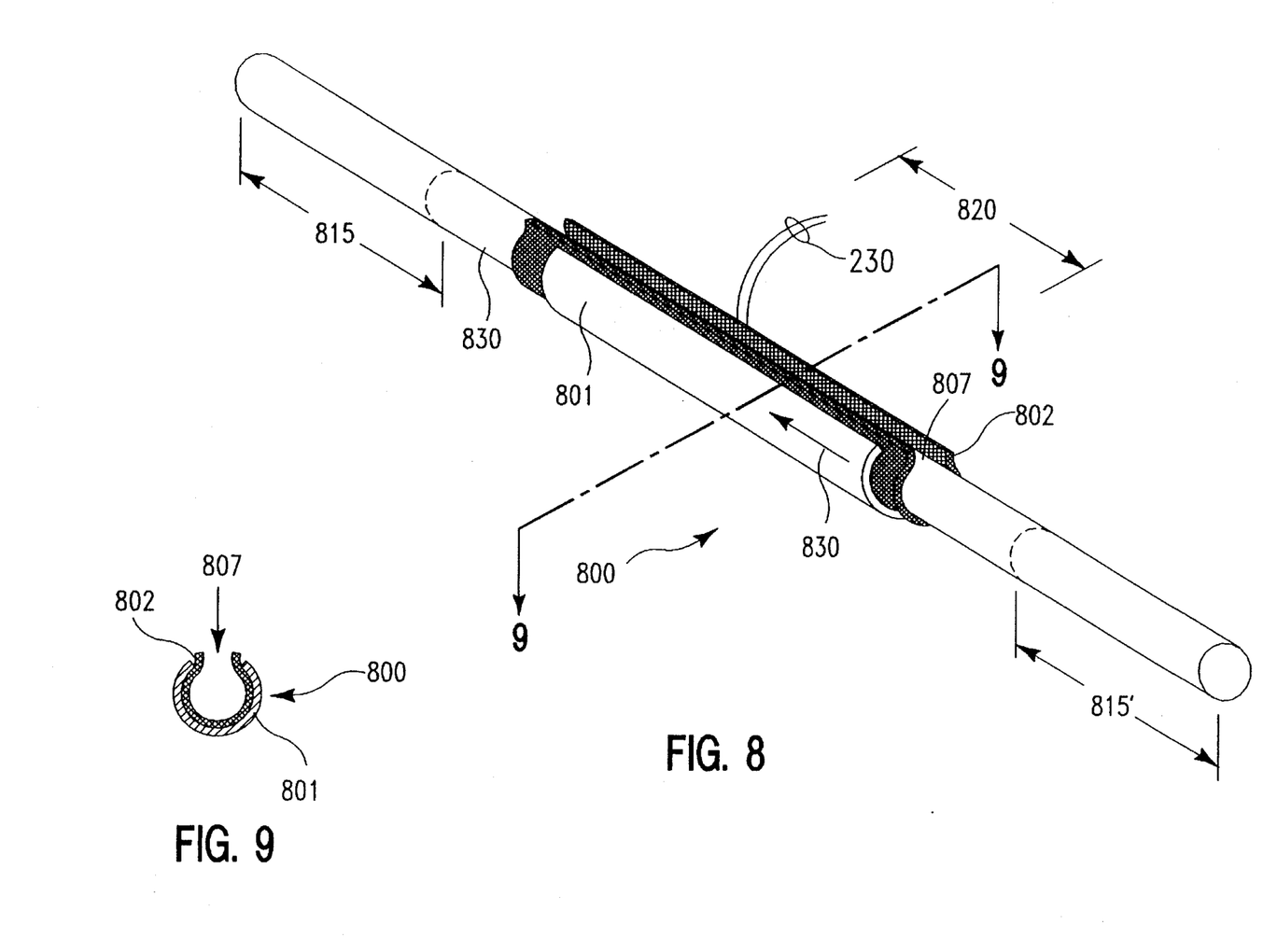
FIG. 8 depicts another embodiment of my inventive crucible, i.e. crucible 800, holding a specimen in the form of a cylindrical bar.
FIG. 9 depicts a cross-sectional view of my inventive crucible 800, the cross-section here being taken along a plane perpendicular to a longitudinal axis of the crucible and containing lines 9—9 shown in FIG. 8 and viewed in the direction of arrow 830 shown therein.

FIG. 8 depicts a further embodiment of my inventive crucible for holding a specimen in the form of a cylindrical bar. To facilitate understanding, throughout the following discussion, the reader should also simultaneously refer to FIG. 9 which shows a cross-sectional view of this crucible.

Here, specimen 830 is in the shape of a cylindrical bar having a round cross-section. The specimen has ends 815 and 815' which are gripped in the jaw assemblies, as described above but with complementary round rather rectangular channels. Crucible 800 is formed of insulating material 802, held in place by shell 801, both of these items being manufactured of the corresponding material described above. Crucible 800 does not contain a flange with a removal hole, as described above, for two reasons: the crucible essentially surrounds the entire cross-section of the specimen and thus, after deformation, can not be readily removed; and round cylindrical shaped specimens will generally not be used to simulate processes that require rapid cooling.

Insulating material 802, which surrounds specimen 830, may initially be tubular or a flat sheet, the latter with a joint cut at slot 807. This slot permits the specimen to be compressed, through its ends, by inward relative movement of the jaw assemblies (see FIG. 1) while central region 820, shown in FIGS. 8 and 9, of the specimen is liquid. This compression is required to compensate for shrinkage in the size of the specimen as the liquid portion of the specimen within region 820 fills small spaces present in the "fit", on one side, between insulating material 802 and the specimen itself and, on the other side, between shell 801 and the insulating material. The amount of resulting "fill" that occurs, while quite small, is enough to cause a depression in the top of the specimen in region 820. As such, this compression of the specimen causes the molten liquid to fill in the depression, that would otherwise remain, and to conform region 820 to the shape of the crucible, up to slot 807— thereby providing a bar with a fully round cross-section upon subsequent solidification. In most cases, this compression is continued until slot 807 is either completely or partially filled with molten liquid.

Shell 801 may be a tube with slot 807 cut into one side and along the length of the tube, or a flat sheet rolled into the form of a tube with a gap between the ends of the sheet to form the slit.

Though the shell has been described as being thin, illustratively 0.88 mm thick in the preferred embodiment, the thickness of the shell is not critical provided the shell is easily deformable and possesses a relatively large exposed surface area and relatively small mass to facilitate heat loss. Though the specimen is shown in the form of a linear bar, either of rectangular or circular cross-section, the specimen might, in certain instances, take on other shapes rather than a simple linear bar. In that case, the crucible, particularly both the insulating material and the shell, would be shaped to correspondingly conform to the shape of the specimen then in use and then properly oriented on the specimen to contain liquid and/or semi-solid portions thereof. If needed, an appropriate external support would the hold the crucible in position on the specimen.

Furthermore, although I have described the specimen as being deformed, specifically compressed, along its longitudinal axis, the specimen, while being held by my inventive crucible, can be deformed in the GLEEBLE 2000 system cross-wise, i.e., along its transverse axis to provide plane strain. In this case, heating current would still flow axially, in the longitudinal direction, through the specimen. This type of deformation, i.e., plane strain applied cross-wise compression, very closely reproduces the effects of a rolling process undertaken in a mill.

In particular, with longitudinal deformation, the steepest thermal gradients in the specimen occur along the longitudinal axis of the specimen. In various simulation work, such as simulating a rolling process(es), it is beneficial to deform the specimen cross-wise, or in a direction parallel to smaller thermal gradients. My inventive crucible provides, as discussed above, some insulation to heat loss in the specimen and hence reduces the cross-wise thermal gradients that would otherwise occur if that specimen, rather than being held by the crucible, were to be directly exposed to an atmosphere, e.g., air or inert gas. Consequently, by using my inventive crucible to hold a specimen, such specimens can be studied under differing cross-wise thermal gradients: very small gradients, if the crucible remains in place in the specimen; medium gradients, if the crucible is appropriately removed and the specimen surfaces exposed to the atmosphere; and steep thermal gradients, if the crucible is appropriately removed and a suitable coolant is directed at the specimen surfaces. In addition, for these studies, the mode of deformation may be changed from longitudinal tension or compression to plane strain compression.

To provide plane strain compression, the specimen is still longitudinally gripped by two opposing jaw assemblies, as described above. However, and in addition, two rectangular anvils (well known and not shown) are used to compress the specimen along its smallest section dimension in a mid-span or workzone of the specimen. For example, if the specimen is 10 mm (approximately 0.39 inches) by 20 mm (approximately 0.79 inches) in height and width, its length being irrelevant, then the specimen would be cross-wise compressed in the 10 mm direction. In this case, each rectangular anvil may have a flat face 15 mm (approximately 0.59 inches) wide by 30 mm (approximately 1.18 inches) long. Compressing this specimen between two such opposing anvils with the 30 mm dimension of the anvil faces oriented across the specimen, with approximately 5 mm of each anvil extending beyond the specimen edges on each side of the specimen, will cause the specimen to lengthen in an axial direction perpendicular to both its longitudinal axial direction and the axial direction of cross-wise compression. In particular, a flat compressed section will occur 15 mm along the longitudinal axis of the specimen causing the specimen to increase slightly (spread), axially, in the 20 mm direction.

When plane strain is applied in cross-wise compression, both rectangular anvils are electrically insulated from the specimen to prevent heating current from flowing through these anvils. However, thermal currents do flow through both anvils. The amount of this flow, and hence the thermal gradients established thereby, depends upon the anvil temperature relation to the specimen temperature and the thermal conductivity of these anvils.

Although various embodiments which incorporate the teachings of the present invention have been shown and described in detail herein, those skilled in the art can readily devise many other varied embodiments that still incorporate these teachings.

I claim:

1. A crucible usable in combination with a thermal-mechanical material testing system wherein the system holds an electrically conductive test specimen between two axially aligned opposing assemblies, first and second ends of the specimen being securely held by corresponding first and second ones of the assemblies, the system passing electrical heating current serially through the first one of said assemblies, the specimen and the second one of the assemblies to controllably and self-resistively heat the specimen such that a central region of the specimen becomes semi-solid, and the system controllably deforming the specimen while the central region of the specimen is semi-solid, and wherein the crucible holds the specimen while both the specimen is self-resistively heated to where the central portion attains a semi-solid state and the specimen is subsequently deformed, the crucible comprising:

an elongated deformable shell having an upwardly directed opening therein and a suitable cross-section shape axially along the shell and in conformity with the shape of the specimen such that the shell is securely positionable over said specimen to confine the central region thereof; and an electrically and thermally insulating flexible layer interposed between and in abutting contact with both said specimen and the shell, said layer having a cross-sectional shape substantially identical to that of the shell but extending beyond the shell so as to thermally insulate the shell from self-resistive heat generated in the specimen and to prevent current from flowing in the shell;

wherein the insulating flexible layer is capable of developing a sufficiently large thermal gradient thereacross such that, when the central region of the specimen located on one side of the insulating layer is at a liquid temperature, the temperature of the shell at a location on a opposing side of the layer remains sufficiently below a liquidus temperature of the shell so that the shell possesses sufficient mechanical strength to mechanically support the central region of the specimen and wherein the insulating flexible layer has a maximal porosity such that substantially no liquefied specimen material in the central region permeates through the insulating flexible layer and contacts the shell.

2. The crucible recited in claim 1 wherein the insulating flexible layer, when situated between said specimen and the shell, has a length and a height which exceeds the length and height, respectively, of the shell.

3. The crucible recited in claim 2 further comprising:

a fastener which attaches the insulating flexible layer to the shell;

a flange outwardly and downwardly extending across at least a portion of a lower edge of the shell; and a hole formed in the flange, said hole being capable of engaging with a puller so as to permit the crucible to be removed from the specimen while the specimen is being held by said first and second assemblies.

4. The crucible recited in claim 2 wherein the shell and the insulating flexible layer both have a U-shaped cross-sectional shape and each extends completely across and axially beyond the central region and towards both the first and second ends of the specimen.

5. The crucible recited in claim 4 wherein the insulating flexible layer is a woven silica cloth.

6. The crucible recited in claim 4 wherein the shell is formed of carbon steel or stainless steel.

7. The crucible recited in claim 4 wherein the shell is formed of the same material as the specimen.

8. The crucible recited in claim 4 wherein the shell is formed of a material having a lower melting temperature than that of the specimen.

9. The crucible recited in claim 4 further comprising:

a fastener which attaches the insulating flexible layer to the shell;

a flange outwardly and downwardly extending across at least a portion of a lower edge of the shell; and a hole formed in the flange, said hole being capable of engaging with a puller so as to permit the crucible to be removed from the specimen while the specimen is being held by said first and second assemblies.

10. The crucible recited in claim 4 wherein the shell is formed of stainless steel sheet having a thickness of 0.034 inch (0.88 mm) and said insulating flexible layer is the woven silica cloth having a thickness of 0.029 inch (0.75 mm).

11. The crucible recited in claim 2 wherein the shell and the insulating flexible layer both have a circular shaped cross-sectional shape and each extends completely across the central region of the specimen, the shell and the insulating flexible layer both having a open slot therein laterally extending across a corresponding top surface thereof.

12. The crucible recited in claim 11 wherein the insulating flexible layer is a woven silica cloth.

13. The crucible recited in claim 11 wherein the shell is formed of carbon steel or stainless steel.

14. The crucible recited in claim 11 wherein the shell is formed of the same material as the specimen.

15. The crucible recited in claim 11 wherein the shell is formed of a material having a lower melting temperature than that of the specimen.

16. The crucible recited in claim 11 wherein the shell is formed of stainless steel sheet having thickness of 0.034 inch (0.88 mm) and said insulating flexible layer is the woven silica cloth having a thickness of 0.029 inch (0.75 mm).

* * * * *